United States Patent
Kohane et al.

(10) Patent No.: US 8,410,297 B2
(45) Date of Patent: Apr. 2, 2013

(54) PROCESS FOR PRODUCING ORGANOHALOHYDROSILANES

(75) Inventors: Joseph Peter Kohane, Indianapolis, IN (US); Unnikrishnan R. Pillai, Union, KY (US); Jonathan David Wineland, Bedford, KY (US)

(73) Assignee: Dow Corning Corporation, Midland, MI (US)

( * ) Notice: Subject to any disclaimer, the term of this patent is extended or adjusted under 35 U.S.C. 154(b) by 14 days.

(21) Appl. No.: 13/141,363

(22) PCT Filed: Dec. 14, 2009

(86) PCT No.: PCT/US2009/067803
§ 371 (c)(1),
(2), (4) Date: Jun. 22, 2011

(87) PCT Pub. No.: WO2010/075013
PCT Pub. Date: Jul. 1, 2010

(65) Prior Publication Data
US 2011/0257422 A1    Oct. 20, 2011

Related U.S. Application Data

(60) Provisional application No. 61/140,193, filed on Dec. 23, 2008.

(51) Int. Cl.
C07F 7/12        (2006.01)
(52) U.S. Cl. ............... 556/472; 556/473; 556/469
(58) Field of Classification Search .......... 556/472, 556/473, 469
See application file for complete search history.

(56) References Cited

U.S. PATENT DOCUMENTS

| | | | |
|---|---|---|---|
| 3,132,168 A | 5/1964 | Mackinnon | |
| 3,155,698 A | 11/1964 | Nitzsche et al. | |
| 3,505,379 A | 4/1970 | Bonitz | |
| 3,775,457 A | 11/1973 | Muraoka et al. | |
| 4,115,426 A * | 9/1978 | Hiiro et al. | 556/474 |
| 4,602,101 A | 7/1986 | Halm et al. | |
| 4,656,301 A | 4/1987 | Prud'Homme et al. | |
| 4,762,940 A | 8/1988 | Halm et al. | |
| 4,965,388 A | 10/1990 | Halm et al. | |
| 4,973,725 A * | 11/1990 | Lewis et al. | 556/472 |
| 5,728,858 A | 3/1998 | Lewis et al. | |
| 5,777,146 A | 7/1998 | Straussberger et al. | |
| 7,202,192 B2 | 4/2007 | Colin | |
| 7,238,638 B2 | 7/2007 | Colin | |
| 2007/0244337 A1 | 10/2007 | Colin | |
| 2007/0249855 A1 | 10/2007 | Kanner | |
| 2007/0264182 A1* | 11/2007 | Vajo et al. | 423/286 |

OTHER PUBLICATIONS

Chiao Ku; Material Engineering thesis; Carbon nanotubes for hydrogen storage; Nov. 31, 2002.*
Bowden et al; Journal of American Chemical Society, 1934, 56(3) 689-691.*

* cited by examiner

Primary Examiner — Sudhakar Katakam
Assistant Examiner — Pancham Bakshi
(74) Attorney, Agent, or Firm — Catherine U. Brown

(57) ABSTRACT

The invention pertains to a method of producing organohalohydrosilanes by treating a silicon metal with a halogen-containing compound, wherein the halogen-containing compound has a formula selected from $R_dSiX_{4-d}$ (II) and RX (III), combining a catalyst and a promoter with the treated silicon metal, and contacting the combination with hydrogen gas and an organohalide. The invention also pertains to a method of producing organohalohydrosilanes by contacting an organohalide and hydrogen gas with a combination of silicon metal, a catalyst, a promoter and a hydrogen storage material. The invention also pertains to a method of producing organohalohydrosilanes by contacting an organohalide and hydrogen gas with a combination of a silicon metal, a catalyst, a promoter and a hydrogenation catalyst. The invention also pertains to a method of producing organohalohydrosilanes by contacting an organohalide and hydrogen gas with a reaction mass residue and optionally a hydrogenation catalyst.

17 Claims, No Drawings

US 8,410,297 B2

PROCESS FOR PRODUCING ORGANOHALOHYDROSILANES

CROSS-REFERENCE TO RELATED APPLICATIONS

This application is a U.S. national stage filing under 35 U.S.C. §371 of PCT Application No. PCT/US09/67803 filed on Dec. 14, 2009, currently pending, which claims the benefit of U.S. Provisional Patent Application No. 61/140,193 filed Dec. 23, 2008, under 35 U.S.C. §119 (e). PCT Application No. PCT/US09/67803 and U.S. Provisional Patent Application No. 61/140,193 are hereby incorporated by reference.

BACKGROUND OF THE INVENTION

Silanes are useful in diverse industries from construction to automotive, marine to sporting goods, and electronics to aerospace. In these industries, silanes function as, among other things, coupling agents, adhesion promoters, stabilizers, hydrophobing agents, dispersing agents, moisture scavengers, and crosslinking agents. In addition to being useful alone, silanes may function as the building blocks of other materials such as silicones.

Silanes are typically made commercially by what is commonly known as the "direct process." The direct process was first introduced by Rochow and has since been modified to optimize and control the silanes produced by the process. Generally, the direct process involves the reaction of silicon metal with an organic halide, such as methyl chloride, in the presence of a metal catalyst and promoters to produce a mixture of silanes. The process can produce halosilanes, organohalosilanes, as well as organohalohydrosilanes, but the predominant silane produced industrially by the direct process is dimethyldichlorosilane. Because the predominant silane produced is dimethyldichlorosilane, there can be shortages of other silanes, and methods of controlling the direct process to produce other silanes besides diorganodihalosilanes are desired.

The present inventors have found a new method to produce organohalohydrosilanes. The method allows better control of the direct process to provide, in some embodiments, increased selectivity for organohalohydrosilanes, improved ratio of the specific organohalohydrosilanes produced, and improved methyl efficiency.

BRIEF SUMMARY OF THE INVENTION

The invention pertains to a method of producing organohalohydrosilanes by treating a silicon metal with a halogen-containing compound, wherein the halogen-containing compound has a formula selected from $R_dSiX_{4-d}$ (II) and RX (III), wherein each R is independently H or a C1-C20 hydrocarbyl group, X is fluoro, chloro, bromo, or iodo, and d is 0, 1, 2, or 3; combining a catalytic effective amount of a catalyst and a promoter with the treated silicon metal, and contacting the combination with hydrogen gas and an organohalide; provided when the halogen-containing compound is hydrogen chloride, the silicon metal is not treated simultaneously with the hydrogen chloride and the catalyst.

The invention also pertains to a method of producing organohalohydrosilanes by contacting an organohalide and hydrogen gas with a combination of silicon metal, a catalyst, a promoter and a hydrogen-storage material.

The invention also pertains to a method of producing organohalohydrosilanes by contacting an organohalide and hydrogen gas with a combination of a silicon metal, a catalyst, a promoter and a hydrogenation catalyst.

The invention also pertains to a method of producing organohalohydrosilanes by contacting an organohalide and hydrogen gas with a reaction mass residue and optionally a hydrogenation catalyst.

DETAILED DESCRIPTION OF THE INVENTION

The method pertains to the production of organohalohydrosilanes having general formula (I):

$$R_aH_bSiX_c \qquad (I)$$

wherein each R is independently a C1-C20 hydrocarbyl group, a C1-C12 hydrocarbyl group, a C1-C6 hydrocarbyl group, an ethyl group, or a methyl group; X is fluoro, chloro, bromo, or iodo; a, b, and c are each the integers 1 or 2; and a+b+c=4.

Formula (I) encompasses the formulas $RH_2SiX$, $RHSiX_2$ and $R_2HSiX$, wherein R and X are as defined above. Specific examples of organohalohydrosilanes of formula (I) include methylchlorodihydrosilane, methyldichlorohydrosilane, dimethylchlorohydrosilane, ethylchlorodihydrosilane, ethyldichlorohydrosilane, diethylchlorohydrosilane, methylbromodihydrosilane, methyldibromohydrosilane, dimethylbromohydrosilane, methyliododihydrosilane, methyldiiodohydrosilane, dimethyliodohydrosilane, ethylbromodihydrosilane, ethyldibromohydrosilane, diethylbromohydrosilane, phenylchlorodihydrosilane, phenyldichlorohydrosilane, diphenylchlorohydrosilane.

One embodiment of the invention pertains to a method of producing organohalohydrosilanes by treating a silicon metal with a halogen-containing compound, wherein the halogen-containing compound has a formula selected from $R_dSiX_{4-d}$ (II) and RX (III), wherein each R is independently hydrogen, a C1-C20 hydrocarbyl group, a C1-C12 hydrocarbyl group, a C1-C6 hydrocarbyl group, an ethyl group, or a methyl group, X is fluoro, chloro, bromo, or iodo, and d is 0, 1, 2, or 3. Next, a catalytic effective amount of a catalyst and a promoter are combined with the treated silicon metal. This combination is then contacted with hydrogen and an organohalide. However, when the halogen-containing compound is hydrogen chloride, the silicon metal is not treated simultaneously with the hydrogen chloride and the catalytic effective amount of catalyst.

The invention pertains to a method of producing organohalohydrosilanes by treating a silicon metal with a halogen-containing compound. The silicon metal according to the invention comprises at least 70 to <100 weight % Si, based on the weight of the silicon metal; in another embodiment, the silicon metal comprises at least 95 to <100 weight % Si, based on the weight of the silicon metal. In one embodiment, the silicon metal is chemical grade silicon; in another embodiment, the silicon metal comprises from 98 to <100 weight % Si, based on the weight of the silicon metal; in another embodiment, the silicon metal comprises 98 to 99.99 weight % Si, based on the weight of the silicon metal; and in another embodiment, the silicon metal comprises 98 to 99 weight % Si, based upon the weight of the silicon metal. The silicon metal may comprise other elements identified in the art such as Al, Fe, Ca, Ti, Mn, Zn, Sn, Pb, Bi, Sb, Ni, Cr, Co, and Cd and their compounds. Each of these other elements is typically present from 0.0005 to 0.6 wt % based upon the weight of the silicon metal. One skilled in the art would know how to select a silicon metal of sufficient grade and purity. Chemical grade silicon is available commercially.

The silicon metal is typically in the form of particles. The particle size of the silicon metal may vary. In one embodiment, the mean particle size is from 1 to 200 μm; and in another embodiment, the mean particle size of the silicon metal is from 1 to 100 μm; in another embodiment, from 5 to 50 μm. In one embodiment, it is preferred that the silicon have a particle size mass distribution characterized by a 10th percentile of 2.5 to 4.5 μm, a 50th percentile of 12 to 25 μm, and a 90th percentile of 35 to 45 μm. In a still more preferred embodiment, the particle size mass distribution is characterized by a $10^{th}$ percentile from 1 to 4 μm a $50^{th}$ percentile from 7-20 μm, and a $90^{th}$ percentile from 30-45 μm. The particle size is not essential to the method but helps to optimize the results. One skilled in the art would know how to select a silicon metal particle size to use in the process of the invention depending upon the reactor and the reactants.

As used herein, "particle size mass distribution" is characterized by three percentile sizes. Each percentile describes the particle size diameter in microns below which a mass percentage of the size distribution resides. For instance, "$10^{th}$ percentile" means that 10% of the mass distribution is smaller than the $10^{th}$ percentile size; "$50^{th}$ percentile" means that 50% of the mass distribution is smaller than the $50^{th}$ percentile size; and "$90^{th}$ percentile" means 90% of the mass distribution is smaller then the $90^{th}$ percentile size. It is noted that the "particle size mass distribution" is given by a mass based particle size distribution as measured by sedimentation techniques, or through laser diffraction/scattering processes with appropriate correction to sedimentation techniques using particle size standards.

Methods of making silicon metal and of achieving various particle size are known in the art. For example, silicon metal may be obtained by heating silicon dioxide in an electric arc furnace with a carbon source. A desired particle size can be obtained by methods known in the art such as by grinding, roller milling, jet milling, or ball milling to grind silicon lumps. The powdered silicon may be further classified as to particle size distribution by means of, for example, screening or use of mechanical classifiers such as a rotating classifier.

In one embodiment, the halogen-containing compound is according to formula (II):

$$R_d SiX_{4-d} \quad (II)$$

wherein R, X, and d are as defined above. In one embodiment, R is ethyl, methyl, or phenyl; and in another embodiment, R is methyl and X is chloro. In one embodiment, R is ethyl, methyl, or phenyl, and there is <2 weight % of other halogen-containing compounds according to formula (II), based upon the total weight of all chlorine-containing compounds according to formula (II). Examples of halosilanes according to formula (II) are $SiCl_4$, $CH_3SiCl_3$, $(CH_3)_2SiCl_2$, $(CH_3)_3SiCl$, $H_3SiCl$, $(CH_3)HSiCl_2$, $(CH_3)_2HSiCl$, $(CH_3)HSiCl_2$, $H_2SiCl_2$, $HSiCl_3$, and $(CH_3)H_2SiCl$.

In one embodiment, the silicon metal is treated with a halogen-containing compound according to formula (III):

$$RX \quad (III)$$

wherein R, X are as defined above. Examples of compounds according to formula (III) are methyl chloride, ethyl chloride, butyl chloride, benzyl chloride ($C_6H_5CH_2Cl$), methyl bromide, ethyl bromide, butyl bromide, benzyl bromide ($C_6H_5CH_2Br$), hydrogen chloride, and hydrogen bromide. Organohalides and hydrogen halides are available commercially.

The silicon metal is treated with the halogen-containing compounds according to formulas (II) and (III) by methods known in the art. For example, when the halogen containing compound is a gas or a liquid, the silicon metal may be treated by methods known in the art for treating a solid with a gas or a liquid. When the halogen-containing compound is a liquid chlorosilane, the silicon metal may be added to a batch tank and the chlorosilane added to the tank with or without stirring. Or the chlorosilane may be flowed into a bed of silicon metal at room temperature through an inlet such that the silicon metal is brought into contact with the chlorosilane. The chlorosilane may then be drained through an outlet in the tank, or the silicon metal filtered to separate the excess chlorosilane from the silicon metal. After treating with the chlorosilane, the silicon metal may be dried by, for example, putting the silicon metal under a nitrogen gas flow.

When the halogen-containing compound is a gas, such as methyl chloride, the silicon metal may be treated by methods known in the art for treating solids with a gas. For example, the methyl chloride may be passed through a packed bed, fluidized bed, stirred bed or vibrating bed containing the silicon metal via an inlet thereby bringing the silicon metal into contact with the methyl chloride. The excess methyl chloride may then be exhausted or vented out an outlet. One skilled in the art would know how to treat silicon metal with the halogen-containing compound whether a gas or a liquid.

The amount of halogen-containing compound may vary. There really is no limit on the maximum amount of halogen-containing compound which may be used to treat the silicon metal except for those related to cost, time, and other practical considerations. Typically, the silicon metal is treated with enough of the halogen-containing compound to fully wet the silicon metal with the halogen containing compound. As used herein, "wet" is intended to mean that the surface of the metal has been entirely or nearly entirely coated with halogen-containing compound. When the halogen-containing compound is a gas, the silicon metal is treated with enough of the halogen containing compound to completely or nearly completely surround the silicon metal and bring the silicon metal and halogen-containing compound into contact. The silicon metal is typically treated with >1 weight % halogen containing compound, based upon the weight of the silicon metal; in another embodiment, the silicon metal is typically treated with >10 weight % halogen-containing compound, based upon the weight of the silicon metal; in another embodiment, the silicon metal is treated with from 20-250 weight percent halogen-containing compound, based upon the weight of the silicon metal; and in another embodiment, the silicon metal is treated with from 25 to 200 weight % halogen-containing compound, based upon the weight of the silicon metal. One skilled in the art would know how to treat silicon metal with a gas or a liquid according to formula (II) or (III).

The temperature at which the silicon metal is treated with the halogen-containing compound of formula (II) and (III) may vary. The temperature may vary depending upon the identity of the halogen-containing compound. For example, when the halogen-containing compound is according to formula (II), the treatment temperature is typically around room temperature. In one embodiment, the halogen-containing compound is a compound according to formula (II), and the temperature at which the silicon metal is treated is from 15 to 60° C.; in another embodiment, the silicon metal is treated with a compound according to formula (II) at a temperature from 20 to 30° C.; in another embodiment, the silicon metal is treated with a halosilane at a temperature from 22 to 28° C. One skilled in the art would know how to vary the temperature at which silicon metal is treated with a halosilane.

In one embodiment, the silicon metal is treated with a halogen-containing compound according to formula (III) at elevated temperature. In one embodiment, the silicon metal is treated with a halogen-containing compound according to formula (III) at a temperature from 250 to 350° C.; in another embodiment, the silicon metal is treated with a halogen-containing compound according to formula (III) at a temperature from 280 to 320° C.; and in another embodiment, the silicon metal is treated with a halogen-containing compound according to formula (III) at a temperature from 295 to 305° C.: and in another embodiment, the silicon metal is treated with a halogen-containing compound according to formula (III) at a temperature of 300° C. One skilled in the art would know how to vary the temperature at which the silicon metal is treated with a halogen-containing compound according to formula (III).

The pressure at which the silicon metal is treated with the halogen-containing compound may vary. When the silicon metal is treated with a halogen-containing compound according to formula (II), the pressure at which the silicon metal is treated is about atmospheric pressure. In another embodiment, the gauge pressure at which the silicon metal is treated with a compound according to formula (II) is from 101 to 506 kPa. When the silicon metal is treated with a compound according to formula (III), the gauge pressure at which the silicon metal is treated is from 101 to 304 kPa; in another embodiment, the gauge pressure is from 101 to 202 kPa.

The time for which the silicon metal is treated with the halogen-containing compound may vary. In one embodiment, the silicon metal is treated with halogen containing compound for up to 240 minutes; in another embodiment, the silicon metal is treated with the halogen-containing compound for >1 minute; in another embodiment, from 1 minute to 240 minutes; in another embodiment, from 5 minutes to 120 minutes. One skilled in the art would know how to vary the treatment time of silicon metal by the halogen containing compound.

The treated silicon metal is combined with a catalytic effective amount of a catalyst and a promoter. Catalysts known in the art for use in the direct process may be used as catalyst to produce organohalohydrosilanes according to the method. In one embodiment, the catalyst comprises copper or silver metals and their compounds; in another embodiment, the catalyst comprises powdered metallic copper, any copper compound, or mixtures thereof; in another embodiment, the catalyst comprises a copper compound selected from cuprous oxide, cuprous chloride, cupric chloride, copper nitride, copper hydroxide, a copper carboxylate such as copper formate, and mixtures thereof; and in another embodiment, the catalyst is cuprous chloride.

The amount of catalyst may vary. In one embodiment, the catalyst is contacted at a catalytic effective amount. A "catalytic effective amount", as used herein, is intended to mean an amount effective to catalyze the production of the organohalohydrosilane according to the invention. For example, a catalytic effective amount is from 0.01 to about 10 weight % based upon the total weight of the catalyst, silicon metal, and promoter. In one embodiment, the catalyst is contacted at 0.01 to 8 weight % based upon the total weight of the silicon metal, catalyst and promoter; in another embodiment from 2 to 8 weight %, based upon the total weight of the silicon metal, catalyst and promoter. One skilled in the art would know how to adjust the amount of catalyst for the amount of reactants.

The catalyst is typically in the form of particles, and the particle size of the catalyst may vary. In one embodiment, the catalyst has a mean particle size diameter from 1 to 200 µm; in another embodiment, the catalyst has a mean particle size diameter from 1 to 100 µm; and in another embodiment, the catalyst has a mean particle size diameter from 5 to 50 µm. It is known in the art that reaction efficiency improves with lower catalyst particle size. The desired particle size of the catalyst may be achieved by reducing the size of larger particles or by forming the catalyst particles into the desired size when created. Larger size particles of catalyst may be reduced by grinding, ball milling, or any other suitable method known in the art for reducing the particle size of a solid catalyst. Catalyst particles of the desired size may be formed by, for example, atomization.

The catalyst is produced by methods known in the art. For example, the catalyst, where appropriate, may be produced by atomization and partial oxidation of the molten metal, by the partial oxidation of electrolytically or chemically produced metal, or by the incomplete reduction of the metal oxide. Mixtures of copper and copper oxides produced by cementation may contain quantities of Zn, Cd, and Sn. During cementation, an aqueous copper-bearing solution is contacted with Al, Fe, Zn or another metal higher in the electrochemical series than copper. The copper precipitates and the metal dissolves. As a result of partial air oxidation, the precipitate is a mixture of copper, cuprous oxide and cupric oxide. Copper catalysts prepared in this way are known as cement catalysts. Those partially oxidized copper catalysts not so prepared are called non-cement catalysts.

The catalyst may comprise additional elements such as Al, Fe, Ca, Ti, Mn, Zn, Sn, Bi, Sb, Ni, Cr, Co, and Cd and their compounds, which are typically present from 0.0005 to 0.6 wt % based upon the weight of the catalyst. Catalysts suitable for use in the process may be obtained commercially.

A promoter is combined with a catalytic effective amount of a catalyst and treated silicon metal. "Promoter", as used herein, is intended to mean any of the metals and other elements which are known to increase the activity and/or silicon conversion and/or selectivity in the direct process. "Selectivity," as used herein, is intended to mean the weight ratio of certain silanes, such as organohalohydrosilanes to organohalosilanes, diorganohydrohalosilanes to organohydrodihalosilanes; or dimethyldichlorosilane to methyltrichlorosilanes, as produced in the direct process. Examples of metals that are known to function as promoters in the direct process are, for example, tin, zinc, phosphorous, cadmium, cesium, and bismuth.

In one embodiment, the promoter comprises tin, zinc, phosphorous, or a combination thereof. Any promoter present is typically at from 5 to 10,000 parts per million (ppm) based on the weight of silicon metal, catalyst, and all promoters present. In one embodiment, the promoter may comprise one or more of the following in the following amounts: 50 to 10,000 ppm zinc; 5 to 200 ppm tin, antimony or arsenic; 10 to 1000 ppm cesium; and 25 to 2,500 ppm phosphorous, based on silicon metal in the process. The promoter may be introduced into the process as an impurity in the silicon metal, an impurity in the catalyst, separately added, or through some combination of impurity and separate addition. One skilled in the art would know how to determine the amount of promoter in the catalyst and silicon metal and how to contact additional promoter.

Hydrogen and an organohalide are contacted with the combination of treated silicon metal, promoter, and catalysts. The hydrogen is hydrogen gas, $H_2$. The purity of the hydrogen gas may vary. One skilled in the art would know how to select hydrogen of a suitable grade or purity to use in the method. For example, hydrogen that is >99% $H_2$ and impurities, such as water and oxygen, at >25 parts per million (ppm) by weight may be used in the method of the invention. Hydrogen gas of suitable purity is available commercially or may be recovered from other industrial processes or the direct process and redirected or recycled for use herein.

The organohalide is according to formula (III) described above, wherein R is a C1-C20 hydrocarbyl group, a C1-C12 hydrocarbyl group, a C1-C6 hydrocarbyl group, an ethyl group, a phenyl group, or a methyl group, and X is fluoro, bromo, chloro, or iodo.

Examples of organohalides according to formula (III) and useful in the method are methyl chloride, ethyl chloride, and benzyl chloride. In one embodiment, the organohalide is methyl chloride.

One skilled in the art would know how to contact the combination of treated silicon metal, catalyst, and promoter with hydrogen and an organohalide. For example, the hydrogen and organohalide could be contacted via an inlet in a fluidized, stirred, or vibrating bed reactor containing silicon metal, catalyst and promoter. Typically, when hydrogen is fed to the reactor, the hydrogen and organohalide are fed to the reactor simultaneously or nearly simultaneously. The flow rate of the organohalide may vary. There are really no limits on the flow rate of the organohalide except practical limits related to cost, safety, and optimization of the silicon conversion. As a general guide, the flow rate is typically >5 weight % per hour, based upon the weight of the silicon metal; in another embodiment, the flow rate of the organohalide is typically >140 weight % per hour, based upon the weight of the silicon metal; in another embodiment, the flow rate is 5 to 250 weight % per hour, based upon the weight of the silicon metal, catalyst, and promoter; in another embodiment, from 20 to 200 weight % per hour, based upon the weight of the silicon metal, catalyst, and promoter; in another embodiment, the organohalide flow rate is from 100 to 200 weight % per hour, based upon the weight of the silicon metal, catalyst and promoter.

The amount of hydrogen may affect both the selectivity and the silicon conversion. "Silicon conversion", as used herein, is intended to mean the weight of silicon metal reacted divided by the initial silicon metal weight multiplied by 100. In one embodiment, the hydrogen is from 5 to 85 mol %, based upon the moles of hydrogen and organohalide; in another embodiment, the hydrogen is from 5 to 60 mol %, based upon the moles of hydrogen and organohalide; in another embodiment, the hydrogen is from 5 to 40 mol %, based upon the moles of hydrogen and organohalide; in another embodiment, the hydrogen is from 10 to 20 mol %, based upon the moles of hydrogen and organohalide. One skilled in the art would know how to vary the hydrogen content with that of the organohalide.

When the fluidized bed reactor is used, the total amount of hydrogen and organohalide is typically, at a minimum, sufficient to fluidize the silicon metal, catalyst, and promoter particle reactants and less than a flow that completely discharges or elutriates the reactants from the reactor before the silicon particles have reacted. The minimum flow for fluidization may be computed from knowledge of the gas densities, the density and particle size distribution of the silicon metal, and the temperature of the reaction. One skilled in the art would know how to calculate the minimum flow for adequate reactant fluidization. It is possible to operate a fluidized bed above the minimum flow and still keep the silicon metal in the reactor in a fluidized state.

The minimum reactor temperature at which the hydrogen gas and organohalide are contacted with the combination of silicon metal, catalyst, and promoter is set by the initiation temperature of the reaction between the organohalide and the combination. One skilled in the art would know how to determine minimum initiation temperature. Typically, the reactor temperature is from 260 to 320° C.; in another embodiment, from 280 to 315° C.; and in another embodiment, from 300 to 315° C. The maximum acceptable temperature may be determined by the onset of organohalide pyrolysis. Such pyrolysis is usually accompanied by markedly increased formation of byproducts. Temperatures above 380° C. lead to low $R_2SiHX$ formation and/or $R_2SiHX$ decomposition.

The pressure at which the hydrogen and organohalide are contacted with the combination may vary. The contacting may take place at atmospheric or super-atmospheric pressures. It is advisable to conduct the synthesis under pressure since this increases the rate of the reaction and makes more efficient use of the hydrogen, organohalide, and silicon metal. A gauge pressure at or below about 306 kPa assures controllable reaction rates. In one embodiment, the contacting gauge pressure is from 101 to 306 kPa and allows the process to be operated smoothly and controllably at acceptable selectivities.

In another embodiment of the invention, organohalohydrosilanes are produced by contacting a silicon metal with an organohalide and hydrogen gas with a combination of silicon metal, a catalyst, a promoter and a hydrogen-storage material, wherein the hydrogen storage material has been optionally saturated with hydrogen. The organohalohydrosilanes produced are according to formula (I). The organohalide is according to formula (III) described and exemplified in the embodiments above wherein R is a C1-C20 hydrocarbyl group, a C1-C12 hydrocarbyl group, a C1-C6 hydrocarbyl group, an ethyl group, or a methyl group, X is fluoro, chloro, bromo, or iodo. In one embodiment, R is C1-C12 hydrocarbyl group and X is chloro; an in another embodiment, R is methyl and X is chloro. The silicon metal and the hydrogen gas are as described an exemplified in the embodiments above.

The hydrogen-storage material is carbon or a metal hydride. In one embodiment, the hydrogen-storage material is activated carbon having a BET surface area from 500 to 1500 m²/g; in another embodiment, the activated carbon has a BET surface area from 700 to 1400 m²/g; and in yet another embodiment, the activated carbon has a BET surface area from 1000 to 1400 m²/g.

The activated carbon has a particle size, and the particle size may vary. In one embodiment, the particle size of the activated carbon is from 0.1 to 2 mm. Examples of activated carbon useful in the present invention include those sold under the Norit and Darco trademarks by Norit Americas and under the Sabre and Spartan trademarks by Carbon Resources Corporation and meeting the specifications herein described. One skilled in the art would know how to select an activated carbon based upon the BET surface area and particle size.

In one embodiment, the hydrogen-storage material is a metal hydride. In another embodiment, the hydrogen-storage material is the metal hydride $NaBH_4$, $KBH_4$, $Al(BH_4)_3$ or $NaAlH_4$. Metal hydrides such as $NaBH_4$, $KBH_4$, $Al(BH_4)_3$, and $NaAlH_4$ are available commercially. The particle size of the metal hydride is from 10 to 100 μm, from 10 to 50 μm, or from 10 to 30 μm. The metal hydrides also do not fully decompose at the reaction temperatures herein described.

The hydrogen-storage material is combined with the silicon metal, catalyst and promoter, and contacted with the hydrogen and organohalide by methods known in the art. For example, the silicon metal, the catalyst, the promoter, and the hydrogen-storage material may be added to a shaker and then shaken together until thoroughly mixed, or added together to a vibrating or stirred bed and mixed. One skilled in the art would know how to mix the hydrogen-storage material and how to determine when the silicon metal, catalyst, promoter and hydrogen-storage material is thoroughly mixed.

In one embodiment, the hydrogen-storage material optionally is saturated with hydrogen gas before combining with the silicon metal, catalyst, and promoter and then contacting with the organohalide and hydrogen gas. "Saturated", as used herein, is intended to mean that the hydrogen-storage material has been contacted with hydrogen for a period of time to achieve maximum adsorption of the hydrogen gas. For example, the hydrogen-storage material may be saturated with hydrogen gas by contacting the hydrogen-storage material with hydrogen for >1 seconds. In one embodiment, the hydrogen-storage material is saturated with hydrogen gas by contacting hydrogen with the hydrogen-storage material for up to 4 hours; in another embodiment, the hydrogen-storage material is contacted with hydrogen gas for 1 second to 4 hours; in another embodiment, the hydrogen-storage material is saturated with hydrogen gas for 5 minutes to 2 hours. The contacting of the hydrogen storage material may be conducted by introducing hydrogen gas to the hydrogen-storage material by, for example, flowing hydrogen gas into a reservoir or a mixing tank containing the hydrogen-storage material.

The temperature at which the hydrogen-storage material is saturated with hydrogen gas may vary. The hydrogen gas may be from ambient to 400° C., from 100 to 300° C., or from 250 to 300° C. Similarly, the hydrogen-storage material may be from ambient to 400° C., from 100 to 300° C., or from 250 to 300° C. When the hydrogen-storage material is contacted at temperatures above ambient, the hydrogen-storage material is typically heated by nitrogen gas flow at an elevated temperature. When the hydrogen-storage material is at elevated temperature, it may be contacted with hydrogen gas at ambient temperature to bring the hydrogen-storage material to ambient temperature. One skilled in the art would know how to adjust the temperature at which the hydrogen-storage material and hydrogen are contacted.

The pressure at which the hydrogen-storage material is saturated with hydrogen may vary. The hydrogen-storage material may be saturated with hydrogen at atmospheric pressure or super-atmospheric pressure. For optimal performance, the hydrogen-storage material is saturated with the hydrogen at super-atmospheric pressure. In on embodiment, the hydrogen-storage material is saturated with hydrogen at a pressure of 101 kPa to 306 kPa gauge; in another embodiment, from 101 kPa to 202 kPa gauge; in another embodiment, from 101 kPa to 105 kPa gauge. One skilled in the art would know how to modify the pressure at which the hydrogen-storage material and hydrogen are contacted.

When the hydrogen-storage material is saturated with hydrogen, the time for which the hydrogen-storage material is contacted with hydrogen may vary. The only limit on the time that the hydrogen-storage material is contacted with hydrogen gas is that there must be enough time of the hydrogen-storage material to adsorb or retain a suitable amount of hydrogen. However, as a general guide, the hydrogen-storage material is typically contacted with hydrogen for up to 4 hours; in another embodiment, the hydrogen and hydrogen-storage material are contacted for from 1 minute to 4 hours; in another embodiment, from 5 minutes to 4 hours; in another embodiment, the hydrogen and hydrogen-storage material are contacted for from 1 to 2 hours; in another embodiment, the hydrogen and hydrogen-storage material are contacted for from 1 to 1.5 hours. Contact times longer than 4 hours are generally unnecessary to saturate the hydrogen-storage material with hydrogen as the maximum hydrogen load or adsorption will have already been achieved. As temperature at which the hydrogen-storage material and hydrogen gas are contacted increases the time for which they are contacted may decrease. For example, when contacted at between 250 and 300° C., the contact time is typically from a few minutes to 2 hours. One skilled in the art would know how to vary the contact time of the hydrogen-storage material and hydrogen.

The hydrogen-storage material is combined with the silicon metal, the catalyst, and promoter and the combination contacted with hydrogen and an organohalide. The combination may be contacted with hydrogen and organohalide by feeding the hydrogen gas and organohalide to a reactor containing the combination as described and exemplified herein in earlier embodiments. In this embodiment the hydrogen-storage material has also been combined with the silicon metal, promoter, and catalyst and the silicon metal may or may not have been pretreated as also described and exemplified in earlier embodiments.

The amount of hydrogen-storage material combined with the silicon metal may vary. In one embodiment, the hydrogen-storage material is from 1 ppm to 5 weight %, based upon the weight of the silicon metal, promoter and catalyst; in another embodiment, the hydrogen-storage material is from 0.01 weight % to 4 weight %, based upon the weight of the silicon metal, promoter and catalyst in another embodiment, the hydrogen-storage material is from 0.5 to 4 weight %, based upon the weight of the silicon metal, promoter and catalyst; and, in yet another embodiment, the hydrogen-storage material is from 1 to 2 weight %, based upon the weight of the silicon metal, promoter and catalyst.

In another embodiment, the invention pertains to a method of producing organohalohydrosilanes by contacting an organohalide and hydrogen gas with a combination of a silicon metal, a catalyst, a promoter and a hydrogenation catalyst. The silicon metal, catalyst, promoter, hydrogen and an organohalide are as described and exemplified above in earlier embodiments. The hydrogenation catalyst, as used herein, is meant to include the catalyst as described above, but, is intended to be in addition to the catalyst described above and include any catalyst known in the art for use in hydrogenation chemistry. In one embodiment, the hydrogenation catalyst is copper powder. In another embodiment, the hydrogenation catalyst is a supported metal catalyst. A "supported metal catalyst", as used herein, is intended to mean a catalyst comprising a metal, such as Pd, Pt, Al, and Ni, on a support material known in the art, such as silica gel and activated carbon. One skilled in the art would understand what is meant by a supported metal catalyst. In one embodiment the supported metal catalyst comprises Pd supported on $SiO_2$ such as, for example, 1 weight %, based on the weight of Pd and $SiO_2$, Pd supported on $SiO_2$. In another embodiment, the hydrogenation catalyst is a supported metal catalyst comprising Pt supported on $Al_2O_3$, such as 0.5 weight % Pt, based on the weight of Pt and $Al_2O_3$, supported on $Al_2O_3$. And, in yet another embodiment, the hydrogenation catalyst is a supported metal catalyst comprising 10 weight % Ni, based on the weight of Ni and $Al_2O_3$, supported on $Al_2O_3$. Hydrogenation catalysts are available commercially or may be prepared by traditional catalyst preparation techniques such as impregnation of metal salts on the support followed by calcination and reduction.

The hydrogenation catalyst is typically in the form of particles. The size of the particles may vary. In one embodiment, the hydrogenation catalyst has a particle size from 1 nanometer (nm) to 250 μm; in another embodiment, the hydrogenation catalyst has a particle size from 1 nm to 100 μm in another embodiment, the hydrogenation catalyst has a particle size from 1 nm to 200 nm; in another embodiment, the hydrogenation catalyst has a particle size from 5 to 100 nm; in yet another embodiment, the hydrogenation catalyst has a particle size from 20 to 50 nm.

In one embodiment, the hydrogenation catalyst is present at from 0.1 to 2 weight % based upon the weight of the silicon metal, catalyst, promoter, and hydrogenation catalyst; in another embodiment, the hydrogenation catalyst is present at from 0.2 to 1 weight % based upon the weight of the silicon metal, catalyst, promoter, and hydrogenation catalyst; in another embodiment, the hydrogenation catalyst is present from 0.2 to 0.8 weight % based upon the weight of the silicon metal, catalyst, promoter, and hydrogenation catalyst; and in another embodiment, the hydrogenation catalyst is present at about 0.6 weight % based upon the weight of the silicon metal, catalyst, promoter, and hydrogenation catalyst.

The hydrogenation catalyst is added to the silicon metal, catalyst, and promoter as described above for the catalyst. One skilled in the art would know how to combine hydrogenation catalyst with silicon metal, catalyst, and promoter.

In another embodiment of the invention, a reaction mass residue is contacted with an organohalide and hydrogen. The "reaction mass residue," as used herein, is intended to mean the material remaining in the bed of a reactor after the direct process reaction between silicon metal and an organohalide (or hydrogen halide) in the presence of catalyst and promoter, as described and exemplified above, when the selectivity and product yield are no longer commercially attractive. One skilled in the art would know when the product yield and selectivity are no longer commercially attractive and when the reaction mass residue is formed. The reaction mass residue may contain catalyst such as copper, unreacted organic halide, metals such as silicon, copper, zinc, and aluminum, silicon oxides, carbon residues, impurities, and reaction product. Typical reaction mass residue comprises mainly silicon metal and silicon oxides, and minor amounts of copper catalyst, iron, carbon, aluminum chloride, methyl chloride, and chlorosilanes and polysilanes.

The time to form the reaction mass residue by contacting silicon metal, a catalyst, and a promoter with an organohalide in the direct process may vary. One skilled in the art would know when the reaction mass residue has been formed, and there is really no upper limit on the time to form the reaction mass residue by the direct process. As a general guide, the reaction mass residue may be formed after contacting for >20 hours of conducting the direct process reaction; in another embodiment, the reaction mass residue is created after contacting for >36 hours; in another embodiment, the reaction mass residue is created after contacting for >72 hours; and in yet another embodiment, the reaction mass residue is created after contacting for from 20 hours to 60 days. One skilled in the art would understand what reaction mass residue is and when and how it is created.

The hydrogen gas and organohalide contacted with the reaction mass residue are as described above for contacting with the silicon metal, catalyst, and promoter. The organohalide contacted is according to formula (III), wherein R is a C1-C20 hydrocarbyl group, a C1-C12 hydrocarbyl group, a C1-C6 hydrocarbyl group, an ethyl group, a phenyl group, or a methyl group, and X is fluoro, bromo, chloro, or iodo.

The reaction mass residue is contacted with hydrogen and an organohalide in the same manner as described above for contacting hydrogen gas and an organohalide with silicon metal, a catalyst, and a promoter. The hydrogen gas and organohalide are fed simultaneously or nearly simultaneously to a suitable reactor, such as a packed, fluidized, vibrating or stirred bed reactor, containing the reaction mass residue. The hydrogen gas and organohalide are fed to the reactor under the same conditions and in the same quantities as described above for contacting with silicon metal, catalyst and promoter.

In one embodiment, the reaction mass residue is combined with a hydrogenation catalyst and contacted with hydrogen gas, and organohalide. The hydrogenation catalyst is as described and exemplified above. In one embodiment the catalyst is cuprous chloride or copper powder and is at from 0.1 to 10 weight %, based upon the weight of the reaction mass residue; in another embodiment, from 0.2 to 0.8 weight %, based upon the weight of the reaction mass residue; and in yet another embodiment, 0.6 weight % based upon the weight of the reaction mass residue.

The reaction mass residue and hydrogenation catalyst are combined by methods known in the art. For example, the reaction mass residue and the hydrogenation catalyst can be added together and mixed in a shaker. Or the reaction mass residue and hydrogenation catalyst may be added together to a packed, fluidized, stirred, or vibrating bed reactor. One skilled in the art would know how to combine the reaction mass residue and the hydrogenation catalyst. Once the reaction mass residue and the hydrogenation catalyst are combined, the hydrogen gas and organohalide may be contacted with the reaction mass residue and hydrogenation catalyst as described above for the contacting of the hydrogen gas and organohalide with the reaction mass residue alone.

Separation of the reactants and products according to the invention can be conducted by methods known in the art. For example, solids can be separated from gases via cyclones and/or filters, liquids from solids via filtration, and liquids from liquids and gases from distillation.

The method of the present invention improves the selectivity for products according to formula (I) over silanes not according to formula (I) and for diorganohalohydrosilanes over organodihalohydrosilanes, and, when $CH_3Cl$ is the organohalide, dimethylchlorohydrosilane over methyldichlorohydrosilane. Silanes according to formula (I) produced by the method are represented herein, in total, by the formula SiH, and silanes not according to formula (I) are represented herein, in total, by the formula RSiX. "SiH" as used herein, is intended to mean a silane comprising a silicon to hydrogen bond and includes compounds of formula $R_2HSiCl$ and $RHSiCl_2$. The selectivity of silanes according to formula (I) (SiH) compared to those that are not (RSiX) is represented herein by the weight % ratio SiH/RSiX. Among silanes according to formula (I) produced when $CH_3Cl$ is the organohalide, the selectivity for dimethylchlorohydrosilane (referred to herein as "DM") over methyldichlorohydrosilane (referred to herein as "MD") is represented by the weight % ratio DM/MD (product selectivity DM/MD).

In some, but not necessarily all, embodiments of the invention, the method improves product selectivity SiH/RSiX. In one embodiment, the method produces product with selectivity SiH/RSiX greater than 0.05; in another embodiment, the product selectivity SiH/RSiX is >0.10; in another embodiment, the product selectivity SiH/RSiX is >0.40; in another embodiment, the product selectivity SiH/RSiX is from 0.05 to 1.0; in another embodiment, the product selectivity SiH/RSiX is from 0.1 to 0.95; in another embodiment, the product selectivity SiH/RSiX is from 0.4 to 0.95.

In some, but not necessarily all, embodiments of the invention, the product selectivity DM/MD is improved. In one embodiment, the method produced DM and MD with a product selectivity DM/MD greater than 0.10; in another embodiment, the product selectivity DM/MD is greater than 0.30; in another embodiment, the product selectivity DM/MD is greater than 0.45; in another embodiment, the product selectivity DM/MD is from 0.10 to 1.5; in another embodiment, the product selectivity DM/MD is from 0.45 to 1.25; in another embodiment, the product selectivity DM/MD is from 0.5 to 1.10.

In addition to improving selectivity, the method, in some embodiments, also improves the methyl efficiency. "Methyl efficiency," as used herein, is intended to mean the ratio of total moles of methyl groups to the total moles of chlorine (total moles $CH_3$/total moles Cl) in the products of the method as determined by gas chromatography when methyl chloride is the starting organohalide. Not to be bound by theory, methyl efficiency is a measure of the source of the H in the silicon-hydrogen bonds and how SiH compounds are produced in the process. It is believed that in some processes, the methyl, or organo, groups on the product silane or reactants can decompose to contribute a hydrogen to a silane. However, this route to the production of SiH is undesirable, because it leads to the formation of undesirable byproducts. Therefore, since chlorine and methyl are both contributed to the product from the same reactant methyl chloride, the ratio of methyl to chlorine in the product is a measure of methyl group degradation by the process and formation of byproducts.

In some, but not necessarily all, embodiments of the invention, the methyl efficiency (Me/Cl mole ratio) is improved by the process. In one embodiment, the methyl efficiency is greater than 0.75; in another embodiment, the methyl efficiency is greater than 0.80; in another embodiment, the methyl efficiency is greater than 0.95; in another embodiment, the methyl efficiency is from 0.75 to 1.00; in another embodiment, the methyl efficiency is from 0.90 to 1.00; in another embodiment, the methyl efficiency is from 0.96 to 0.99.

EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention. All percentages are in weight % unless otherwise noted. Weights are in grams (g). The following list of abbreviations and definitions is presented to aide in the reading of the examples:

| Term/Abbreviation | Meaning |
| --- | --- |
| g | Gram. |
| RSiX | $R_dSiX_{4-d}$ in formula (I) as defined above, wherein R is not H. |
| h and hr | Hours. |
| mol % hydrogen ($H_2$) | Mole percent in reference to hydrogen is the moles of hydrogen divided by the sum of the moles of hydrogen and the moles of organohalide multiplied by 100. |
| SiH | A silane comprising a silicon to hydrogen bond including $R_2HSiCl$ and $RHSiCl_2$. |
| % | Percent. |
| Copper phosphide | $Cu_3P$. |
| Product Selectivity-$Me_2HSiCl/MeHSiCl_2$ | The ratio of the weight percent of $Me_2HSiCl$, based upon all the products of the process, divided by the weight percent $MeHSiCl_2$, based upon all the products of the process, and is defined below as DM/MD. |
| Product Selectivity-SiH/RSiX | The ratio of the weight percent of SiH, based upon all the products of the process, divided by the weight percent of RSiX, based upon all the products of the process. |
| Product Selectivity-D/T | The ratio of the weight percent of D, based upon all the products of the process, divided by the weight percent of T, based upon all the products of the process. |
| Product Selectivity-DM/MD | The ratio of the weight percent of DM, based upon all the products produced by the process, divided by the weight percent of MD, based upon all the products of the process. |
| Me | methyl group ($CH_3$—). |
| Si Conversion | The amount of silicon reacted calculated from the weight of silicon metal reacted divided by the initial silicon metal weight multiplied by 100. |
| Methyl Efficiency or Me/Cl mole ratio | The measure of the methyl group utilization in the process as the ratio of total moles of methyl groups to the total moles of chlorine in the products formed as determined by gas chromatography (GC) using any suitable capillary column capable of separating the various products. |
| D | $(CH_3)_2SiCl_2$ |
| T | $CH_3SiCl_3$ |
| MD | $CH_3HSiCl_2$ |
| DM | $(CH_3)_2HSiCl$ |
| Reaction Mass | The reactants contacted with hydrogen and organohalide including, for example, the silicon metal, the promoter, and the catalyst. |

Example 1 (Comparative)

38.4 g of ground chemical grade (98.5%) silicon, 2.49 g CuCl, 0.0768 g copper phosphide, 0.0018 g Sn and 0.0240 g brass were mixed in a shaker for 30 minutes to form a reaction mass. This reaction mass was transferred to a vibrating carbon steel tubular reactor inserted in an insulated heat shell wrapped with Thermolyne heating tape. The reactor was heated under nitrogen flow at 250° C. for 30 minutes then the temperature was increased to and held between 315-320° C. to maintain a reaction temperature from 300 to 315° C. Methyl chloride (MeCl) was fed into the reactor at a flow rate of 10 g/hr with hydrogen at 20 mol %, based upon the quantity of MeCl and hydrogen. The reactor was vibrated during the reaction using air flow at 22 psig pressure with a pneumatic ball vibrator (Vibco, BBS190) attached to the bottom of the reactor. Products of the reaction were collected by condensation in a dry ice-acetone cooled trap at various time intervals and analyzed by gas chromatography (GC). The results are in Table 1 below. The silicon conversion recorded is after 6 hours after the run for the third entry.

TABLE 1

Direct Process reaction in vibrating bed reactor (VBR) in the presence of hydrogen co-feed.

| Entry | $H_2$ mol % | Time (h) | Product Selectivity | | | Me/Cl Ratio | Si Conversion (%) |
| --- | --- | --- | --- | --- | --- | --- | --- |
| | | | D/T | DM/MD | SiH/RSiX | | |
| 1 | 20 | 2 | 9.5 | 0.43 | 0.21 | 0.92 | 28 |
| 2 | 20 | 4 | 25 | 0.40 | 0.17 | 0.97 | |
| 3 | 20 | 6 | 38 | 0.40 | 0.13 | 0.98 | |

Example 2

The same reactants, conditions, methods, and equipment were used as in example 1 except that two grams of activated carbon with a surface area of 1300 m²/g, were also mixed with silicon metal, catalyst, and promoters, and the hydrogen was co-fed with the methyl chloride and varied at 11, 20, 24, and 33 mol %, based upon the moles of MeCl and hydrogen. The same reaction mass was used for each entry with only the reactant and/or reaction conditions varied as indicated. Therefore, entry 2 represents the results for samples taken 2 hours after the sample for entry 1 was taken. Entry 2 represents a sample taken after a total of 4 hours of run time including the two hours for entry 1. The results are in Table 2 below. The silicon conversion was determined after run 7 and 14 hours of reaction of the same reaction mass, which was used for all entries.

TABLE 2

Gas-solid vibrating bed reaction (VBR) in the presence of hydrogen co-feed and high surface area carbon.

| Entry | $H_2$ mol % | Time (h) | Product Selectivity D/T | DM/MD | SiH/RSiX | Me/Cl Ratio | Si Conversion |
|---|---|---|---|---|---|---|---|
| 1 | 24 | 2 | 5.4 | 1.06 | 0.11 | 0.95 | 49.0 |
| 2 | 24 | 4 | 5.9 | 1.0 | 0.12 | 0.96 | |
| 3 | 20 | 2 | 5.2 | 1.0 | 0.15 | 0.96 | |
| 4 | 11 | 2 | 6.2 | 1.0 | 0.06 | 0.97 | |
| 5 | 11 | 4 | 6.5 | 1.0 | 0.05 | 0.97 | |
| 6 | 33 | 2 | 6.2 | 0.91 | 0.10 | 0.96 | |
| 7 | 33 | 4 | 5.8 | 0.91 | 0.13 | 0.96 | |

Example 2 as compared to comparative example 1 shows the improvement in the product selectivity ratio that can be achieved for MeHSiCl₂ and Me₂HSiCl.

Example 3

The same reactants, conditions, methods and equipment were used as in example 1 except that NaBH₄, was also mixed with silicon metal, catalyst, and promoters at the weight %, based upon the weight of the NaBH₄, silicon metal, catalyst, and promoters. The silicon conversion recorded is after 8 hours. The same reaction mass was used for entries 1-4, and a new reaction mass containing the 0.1 weight % NaBH₄ level was used in entry 5. Entry 3 contains the results for the same reaction mass as entries 1-3 after 6 hours. Entry 4 is the same reaction mass as entries 1-4 and was for samples taken after 2 hours from the sample for entry 3. The results are in Table 2 below.

TABLE 3

Gas-solid vibrating bed reaction (VBR) with hydrogen and sodium borohydride (NaBH₄).

| Entry | Temp (° C.) | Time (h) at each $H_2$ mol % | NaBH₄ (%) | Product Selectivity D/T | DM/MD | SiH/RSiX | Me/Cl Ratio | Si Conversion (%) |
|---|---|---|---|---|---|---|---|---|
| 1 | 310 | 2 | 0.6 | 2.9 | 0.31 | 0.90 | 0.77 | 9.1 |
| 2 | 310 | 4 | 0.6 | 5.3 | 0.47 | 0.48 | 0.90 | |
| 3 | 310 | 6 | 0.6 | 7.0 | 0.48 | 0.33 | 0.92 | |
| 4 | 280 | 2 | 0.6 | 8.1 | 0.47 | 0.12 | 0.94 | |
| 5 | 310 | 6 | 0.1 | 15 | 0.53 | 0.18 | 0.97 | |

The results in Table 3 shows a higher SiH/RSiX selectivity than those in Tables 1-2. These results also show that SiH/RSiX selectivity is decreased and the methyl efficiency is improved by reducing the amount of NaBH₄ used in the reaction (entry 5). The combination of hydrogen and NaBH₄ offers both higher SiH/RSiX and Me₂H/MeH selectivity (DM/MD) than hydrogen co-feed alone as in example 1.

Example 4

The same reactants, conditions, methods and equipment were used as in example 1 except 0.25 g of nano-sized (particle size between 10-50 nm) copper powder were also mixed in a shaker for 30 minutes to form the reaction mass with the silicon, catalyst, and promoter. The results are in Table 4 below. Entry 1 was conducted without tin present, and entry 6 was conducted with regular copper powder (i.e., average particle size from 30 to 50 μm). Entry 2-3 are from the same contact mass with entry 2 representing the results for samples taken after 2 hours and entry 3 after 20 hours reaction. Similarly, entries 4-5 represent samples from the same reaction mass, but after treatment for 6 hours at the differing reaction conditions (i.e., after 6 hours at 20H₂ mol % for entry 4, the mole % H₂ was reduced to 10 for an additional 6 hours). Entry 6 was with a different reaction mass than entries 1-5.

TABLE 4

Effect of addition of nano copper catalyst on SiH generation in the Direct Process reaction in a vibrating bed reactor.

| Entry | Time (h) | Copper catalyst particle size (nm) | Tin Present | $H_2$ (mol %) | Product Selectivity D/T | DM/MD | SiH/RSiX | Me/Cl Ratio | Si Conversion (%) |
|---|---|---|---|---|---|---|---|---|---|
| 1 | 6 | 20-50 | No | 40 | 13 | 0.42 | 0.27 | 0.94 | 25.3 |
| 2 | 6 | 20-50 | Yes | 40 | 16 | 0.55 | 0.11 | 0.96 | 79.4 |
| 3 | 20 | 20-50 | Yes | 40 | 18 | 0.32 | 0.13 | 0.95 | |
| 4 | 6 | 20-50 | Yes | 20 | 20 | 0.5 | 0.13 | 0.97 | 31.5 |
| 5 | 6 | 20-50 | Yes | 10 | 18 | 0.52 | 0.08 | 0.99 | 33.9 |
| 6 | 6 | 3000-5000 | Yes | 40 | 21 | 0.48 | 0.10 | 0.97 | 26.6 |

The results in Table 4 show that omitting tin from the reaction mass enhances SiH/RSiX and DM/MD selectivity. The results also show that methyl efficiency is higher at lower $H_2$ mol %, that additional copper catalyst of particle size from 20 to 50 nm increases silicon conversion over additional copper catalyst of particle size from 30-50 μm, and that added copper catalyst of particle size from 20 to 50 nm increases SiH selectivity over additional copper catalyst of particle size from 30-50 μm.

Example 5

Reaction mass residue was mixed with 0.6 weight % nano copper powder (20-50 nm average particle size) catalyst, based upon the weight of the reaction mass, in a shaker for 30 minutes then transferred to a vibrating carbon steel tubular reactor as described in example 1. The reactor was heated as in example 1 and methyl chloride and hydrogen introduced as in example 1. All other equipment and methods were the same as example 1. The results of the copper addition to the late run samples are shown in Table 5 along with comparative entry 5, where no additional copper was added, and entry 6, where no additional copper was added and the reaction temperature was reduced to 280° C. The silicon conversion recorded is after 20 hours of treatment of entries 1-4 and after treatment for 4 hours for entries 5-6.

TABLE 5

Effect of copper catalyst on SiH generation using reaction mass residue in the Direct Process reaction in a vibrating bed reactor.

| Entry | Time (h) | Product Selectivity D/T | DM/MD | SiH/RSiX | Me/Cl Ratio | Si Conversion (%) |
|---|---|---|---|---|---|---|
| 1 | 2 | 1.3 | 0.61 | 0.49 | 0.76 | 32 |
| 2 | 4 | 2.0 | 0.67 | 0.45 | 0.82 | |
| 3 | 6 | 2.8 | 0.67 | 0.40 | 0.85 | |
| 4 | 20 | 7.7 | 0.91 | 0.12 | 0.95 | |
| 5 (no copper) | 2 | 5.6 | 0.66 | 0.32 | 0.91 | 12 |
| 6 (no copper) | 2 | 11 | 0.53 | 0.14 | 0.96 | |

The results of Table 5 show that the addition of copper catalyst produces high SiH selectivity when hydrogen is co-fed with methyl chloride to a reaction mass residue. The methyl efficiency increases with time with a concurrent decrease in SiH selectivity. The results indicate that methyl efficiency (Me/Cl) increases with decreased temperature (entry 6).

Example 6

Ground chemical grade (98.5%) silicon metal was treated with methyl chloride at 300° C. for 2 hours, HCl and nitrogen at 300° C. for 1 hour, or HCl at 300° C. for 1 hour. The same reactants, conditions, methods and equipment were used as in example 1 except that the methyl chloride or HCl treated silicon metal was substituted for the silicon metal of example 1, and the hydrogen was co-fed with methyl chloride at 54 mol %, based upon the MeCl and hydrogen, for 6 hours. The results are in Table 6 along with comparative entry 2, which also included nitrogen with the HCl treatment. A different reaction mass was used for entries 1-3.

TABLE 6

Effect of silicon pre-treatment on SiH generation in the Direct Process reaction in a vibrating bed reactor.

| | Treatment | | Product Selectivity | | | Si Conversion (%) |
|---|---|---|---|---|---|---|
| Entry | Silicon Treatment | Temperature/ Time | D/T | DM/ MD | SiH/ RSiX | Me/Cl ratio | |
| 1 | MeCl | 300° C./2 h | 13 | 0.76 | 0.08 | 0.98 | 22.7 |
| 2 | $N_2$ + HCl | 300° C./1 h | 15 | 0.58 | 0.01 | 0.98 | 29.2 |
| 3 | HCl | 300° C./1 h | 5.4 | 0.63 | 0.18 | 0.93 | 13.5 |

The results in Table 6 show that treating silicon metal with MeCl at 300° C. for 2 hours before the addition of catalyst and promoters increases the ratio DM/MD during subsequent reaction with MeCl and $H_2$. The results also show that Si pretreatment with HCl enhances SiH and DM/MD selectivity compared to no treatment as in example 1 and that heating Si in a mixture of $N_2$HCl mixture decreases the SiH selectivity compared to heating in HCl alone.

Example 7

Ground chemical grade (98.5%) silicon metal was treated with a mixture of $(CH_3)_2SiCl_2$, $CH_3SiCl_3$, $(CH_3)_3SiCl$, and $CH_3HSiCl_2$ with a D/T ratio of 11.25 and a weight % of $CH_3HSiCl_2$ below 2%, based upon the weight of all chlorosilanes, prior to reaction with hydrogen and methyl chloride by adding the chlorosilane mixture to the silicon metal at room temperature and mixing for 1 to 2 hours, followed by drying the silicon under nitrogen flow overnight. After drying, the chlorosilane treated silicon was used to make the reaction mass of example 1 by substituting 38.4 g of the chlorosilane treated silicon metal for the silicon metal of example 1. The reaction was then conducted with the same reactants, conditions, methods, and reactants as were used as in example 1 except that the mol % of hydrogen co-fed with the methyl chloride was varied and the methyl chloride and hydrogen were fed for varying times. The results are listed in Table 7. Entries 2-3 used the same reaction mass.

TABLE 7

Effect of chlorosilane mixture treated silicon in Direct Process reaction in a vibrating bed reactor.

| Entry | Time (h) | $H_2$ (mol %) | Product Selectivity D/T | DM/MD | SiH/RSiX | Me/Cl Ratio | Si Conv (%) |
|---|---|---|---|---|---|---|---|
| 1 | 6 | 54 | 4.5 | 0.42 | 0.77 | 0.82 | 12.8 |
| 2 | 6 | 46 | 7.1 | 0.33 | 0.52 | 0.86 | 40.9* |
| 3 | 20 | 46 | 14 | 0.25 | 0.32 | 0.89 | |
| 4 | 6 | 30 | 11 | 0.39 | 0.45 | 0.89 | 15.4 |

*Measured after 20 hours.

The results in Table 7 indicate that treatment with a mixture of chlorosilanes leads to higher SiH selectivity.

Example 8

Ground chemical grade (98.5%) silicon metal was treated with methyltrichlorosilane by adding methyltrichlorosilane to the silicon metal at room temperature for 1 to 2 hours. The methyltrichlorosilane was separated from the silicon metal, and the silicon metal dried under nitrogen flow overnight. The same reactants, conditions, methods and equipment were used as in example 1 except that the methyltrichlorosilane treated silicon metal described above in this example was used in place of the silicon metal of example 1, and the feed time of the methyl chloride and hydrogen were varied as indicated with the results in Table 8. Entries 1-5 all used the same reaction mass with samples taken at the various times indicated. The silicon conversion was determined after entry 5 was sampled.

TABLE 8

Effect of methyltrichlorosilane silicon treatment in the Direct Process reaction in a vibrating bed reactor.

| Entry | Time (h) | Product Selectivity | | | Me/Cl Ratio | Si Conversion (%) |
| --- | --- | --- | --- | --- | --- | --- |
| | | D/T | DM/MD | SiH/RSiX | | |
| 1 | 2 | 10 | 0.46 | 0.27 | 0.87 | 60.0* |
| 2 | 4 | 32 | 0.48 | 0.16 | 0.98 | |
| 3 | 6 | 41 | 0.38 | 0.11 | 0.98 | |
| 4 | 8 | 55 | 0.36 | 0.09 | 0.98 | |
| 5 | 20 | 47 | 0.27 | 0.07 | 0.98 | |

*Taken after 20 hours.

As shown in Table 8, the SiH selectivity is better than with no treatment in example 1 at 2 hours, and the DM/MD selectivity is greater at 2 and 4 hours than at the same conditions in example 1. Also, the silicon conversion is 60% after reaction for 20 hours.

That which is claimed is:

1. A method of producing organohalohydrosilanes, comprising:
   treating a silicon metal with a halogen-containing compound,
   wherein the halogen-containing compound has a formula selected from $R_dSiX_{4-d}$ and RX, wherein each R is independently H or a C1-C20 hydrocarbyl group, X is fluoro, chloro, bromo, or iodo, and d is 0, 1, 2, or 3;
   combining a catalytic effective amount of a catalyst and a promoter with the treated silicon metal, and
   contacting the combination with hydrogen gas and an organohalide; provided when the halogen-containing compound is hydrogen chloride, the silicon metal is not treated simultaneously with the hydrogen chloride and the catalyst wherein the catalyst comprises copper or silver metals and their compounds.

2. The method of claim 1 wherein the hydrogen gas is contacted at 5 to 85 mol % based upon the weight of the organohalide and hydrogen gas.

3. The method of claim 1 wherein the treating is for >1 minute.

4. The method of claim 1 wherein the treating is conducted at a temperature from to 250 to 350° C.

5. The method of claim 1 wherein the organohalide is according to formula (III)

$$RX \qquad (III)$$

wherein R is an C1-C20 hydrocarbyl group and X fluoro, chloro, bromo or iodo.

6. The method of claims 1 wherein the halogen-containing compound is i) $CH_3Cl$, ii) $CH_3SiCl_3$, iii) $(CH_3)_2SiCl_2$, iv) $(CH_3)_3SiCl$, v) $SiCl_4$ or a combination of i), ii), iii), iv), and v).

7. A method of producing organohalohydrosilanes, comprising:
   treating a silicon metal with a halogen-containing compound,
   wherein the halogen-containing compound has a formula selected from $R_dSiX_{4-d}$ and RX,
   wherein each R is independently H or a C1-C20 hydrocarbyl group, X is fluoro, chloro, bromo, or iodo, and d is 0, 1, 2, or 3;
   combining the treated silicon metal with
   a catalyst, a promoter, and a hydrogen storage material; and
   contacting an organohalide and hydrogen gas with the combination wherein the catalyst comprises copper or silver metals and their compounds.

8. The method of claim 7 wherein the hydrogen-storage material is carbon or a metal hydride.

9. The method of claim 8 wherein the hydrogen-storage material is carbon and has a surface area from 500 to 1500 m²/g.

10. The method of claim 8 wherein the hydrogen-storage material is $NaBH_4$.

11. The method of claim 7 wherein the hydrogen-storage material is saturated with hydrogen prior to the contacting.

12. A method of producing organohalohydrosilanes according to claim 1, further comprising:
    during combining the treated silicon metal, promoter, and catalyst, adding a hydrogenation catalyst, wherein the hydrogenation catalyst is in addition to the catalyst.

13. The method of claim 12 wherein the hydrogenation catalyst comprises copper and has a particle size from 1 nm to 250 μm.

14. The method of claim 12 wherein the hydrogenation catalyst is a supported metal catalyst.

15. A method of producing organohalohydrosilanes according to claim 1, further comprising:
    contacting an organohalide and hydrogen gas with a reaction mass residue.

16. The method of claim 15 further comprising combining a hydrogenation catalyst with the reaction mass residue.

17. The method of claim 15 wherein the catalyst comprises copper.

* * * * *